United States Patent [19]

Haugen

[11] Patent Number: 5,330,492

[45] Date of Patent: Jul. 19, 1994

[54] SAFETY SCALPEL

[75] Inventor: Doug L. Haugen, Gainesville, Fla.

[73] Assignee: DLH Concepts, Inc., Gainesville, Fla.

[21] Appl. No.: 964,597

[22] Filed: Oct. 21, 1992

[51] Int. Cl.$^5$ ............................................. A61B 17/32
[52] U.S. Cl. ..................................... 606/167; 30/151; 30/162
[58] Field of Search ............... 606/167, 170, 172, 181, 606/182, 185; 30/151, 162, 164, 167, 286, 335; 128/751

[56] References Cited

U.S. PATENT DOCUMENTS

| | | |
|---|---|---|
| 2,735,176 | 2/1956 | Costin . |
| 3,906,626 | 9/1975 | Riuli . |
| 3,943,627 | 3/1976 | Stanley, Jr. ...................... 30/151 |
| 4,091,537 | 5/1978 | Stevenson, Jr. .................. 30/151 |
| 4,414,974 | 11/1983 | Dotson et al. . |
| 4,491,132 | 1/1985 | Aikins . |
| 4,523,379 | 6/1985 | Osterhout et al. . |
| 4,663,846 | 5/1987 | Takeyama . |
| 4,713,885 | 12/1987 | Kelak et al. ...................... 30/335 |
| 4,730,613 | 3/1988 | Gordy . |
| 4,735,202 | 4/1988 | Williams . |
| 4,757,612 | 7/1988 | Peyrot .............................. 30/151 |
| 5,139,507 | 8/1992 | Dolgin et al. ................... 606/167 |

FOREIGN PATENT DOCUMENTS 3722899  1/1989  Fed. Rep. of Germany ...... 606/167

Primary Examiner—Stephen C. Pellegrino
Assistant Examiner—William W. Lewis
Attorney, Agent, or Firm—Saliwanchik & Saliwanchik

[57] ABSTRACT

A surgical instrument comprised of a handle, a blade fixed to the forward end of the handle, and a spring-biased retractable sheath which is received within the handle. A mechanism is provided for retracting the sheath within the handle by depressing a single button on the upper surface of the handle, such that the sheath is retracted against the force of the spring as the button is depressed, and upon release of the button returns the sheath automatically to its released position covering the blade. Additionally, a mechanism is provided for resisting accidental exposure of the blade.

7 Claims, 5 Drawing Sheets

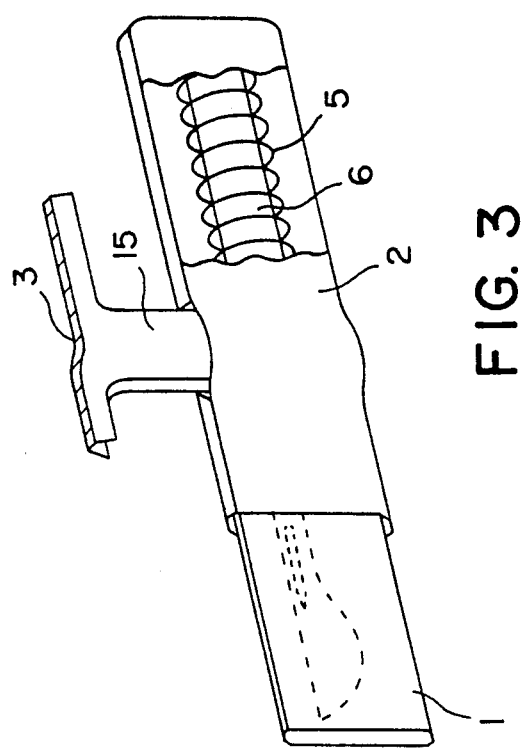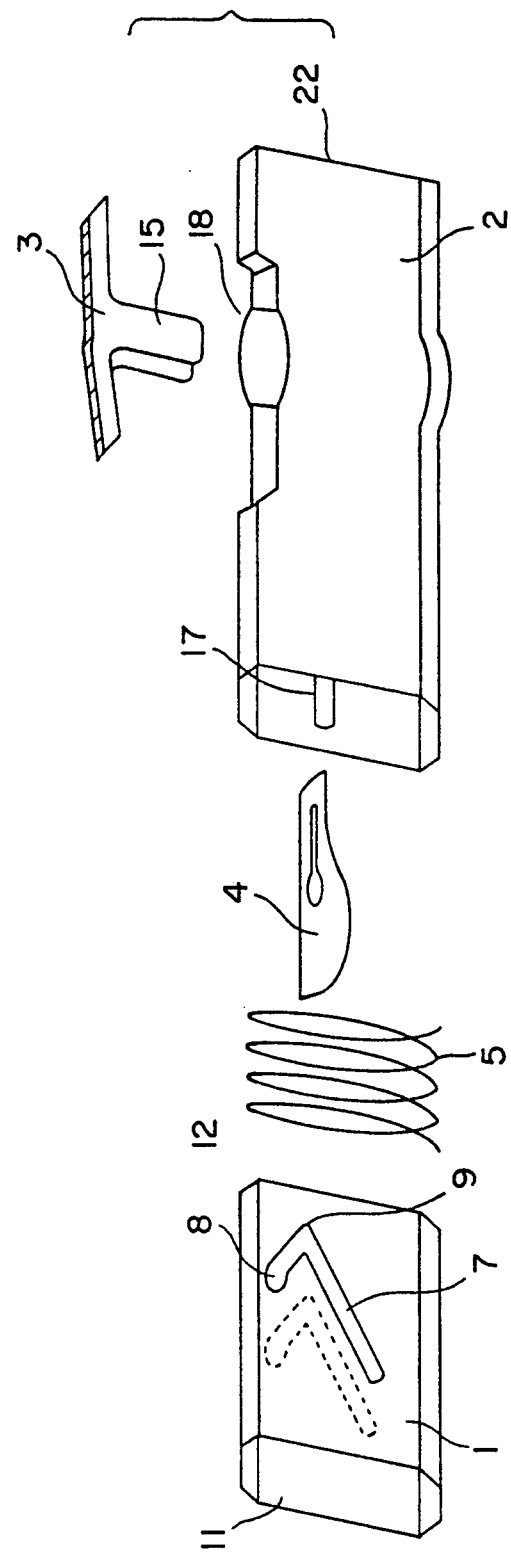

SAFETY SCALPEL

BACKGROUND OF THE INVENTION

1. Field of the Invention

The present invention relates generally to the construction of knives and other sharpened implements. The invention particularly relates to the construction of knives to be used a surgical instruments, and more particularly to the construction of scalpels having an integral cover to protect such implements from damage and from damaging their surroundings.

2. Description of the Prior Art

Surgical scalpels are extremely sharp cutting implements. The extreme sharpness of the blades renders them very hazardous when passing the scalpels back and forth between the surgeon and the operating assistant. It is obvious that extremely sharp scalpels can very easily cut a glove, and the skin beneath the glove; and, if the blade has already been used on a patient, there is an obvious danger of infection. Another difficulty with such extremely sharp knives is that the blades are very easy to ruin, for example, by the scalpel edge coming in contact with another instrument, an instrument tray or other hard surface.

There have been a number of attempts to overcome these problems. U.S. Pat. No. 2,735,176 discloses a veterinary surgical knife which comprises a hollow handle component having a slidably extendable blade. U.S. Pat. No. 4,730,613 and U.S. Pat. No. 4,663,846 disclose cutting instruments having a extendable blades. U.S. Pat. No. 4,491,132 discloses a sheath and a retractable surgical tool combination wherein the blade must be manually extended and retracted in relation to the sheath. U.S. Pat. No. 4,523,379 discloses a knife with retractable sheath, teaching a complex retraction mechanism wherein the sheath must be manually extended to cover the blade, and wherein the blade is exposed when the sheath is in its relaxed position. None of the foregoing are designed to be disposable items U.S. Pat. No. 4,735,202 discloses a disposable microsurgical knife having a locking blade guard which must be manually extended to cover the blade, and, when retracted, is designed to be removed completely from the knife. U.S. Pat. No. 4,414,974 discloses a disposable microsurgical knife having a glow-in-the-dark shroud which must be manually extended to cover the blade and when extended is not locked in place. U.S. Pat. No. 3,906,626 discloses a disposable surgical scalpel in which the sheath must be manually extended to cover the blade, and, once fully extended, is permanently locked in its extended position.

The surgical scalpel of this invention obviates many of the prior art problems. First, its mechanism is simple, inexpensive, and easy to assemble, making it ideal for one-time use. Second, in its released position, the sheath is automatically extended to cover the blade so that manual sheathing of the blade is unnecessary. Third, the blade cannot be accidentally exposed by bumping the sheath. Fourth, the knife can conveniently be simultaneously held and unsheathed with one hand.

SUMMARY OF THE INVENTION

The present invention provides an implement comprising a hollow handle having a knife blade attached at one end. A protective sheath is mounted around the blade and can be retracted into the handle when it is desired to expose the blade. Conveniently, an actuating button is mounted through the top of the hollow handle having a pair of opposed cylindrical protuberances or nipples which engage grooves in the sheath. The sheath is provided with a pair of grooves in the opposed walls thereof, which grooves are received on the nipples connected to the actuating button, and allow the sheath to slide between a fully extended and fully retracted position. Alternatively, the sheath may comprise a cantilevered locking mechanism connected to the actuating button. Normally, the knife will be stored with the sheath in its fury extended, protective position, and various mechanisms are provided for retracting the sheath to expose the blade.

The knife is highly compact and of simple construction, including a particularly reliable sheath retraction mechanism that is easy to actuate, yet resists accidental actuation.

BRIEF DESCRIPTION OF THE DRAWINGS

FIG. 3 is a view of the scalpel shown in FIG. 1, with a cut-away view of the rear interior portion of the handle exposing a preferred placement of the elastic member which is biased to automatically return the sheath to its extended position.

FIG. 4 is an exploded view showing all components of a preferred embodiment of the safety scalpel.

DETAILED DESCRIPTION OF THE INVENTION

Figure 1:
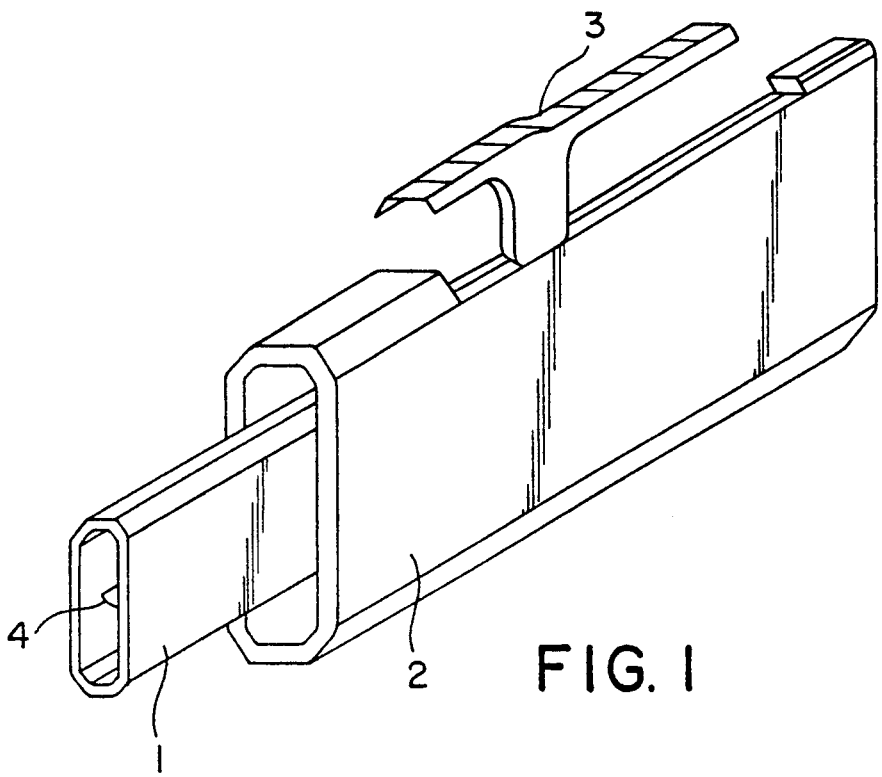
FIG. 1 is a view of a scalpel constructed in accordance with the present invention illustrating a fully extended sheath.

The apparatus of the invention is conveniently fabricated by conventional and standard methods for preparing surgical scalpels using conventional and standard materials. For example, the blade component of the surgical scalpel may be standard surgical steel blades of various shapes which are conventionally employed. The handle and sheath component may be fabricated from conventional polymers such as, for example, polystyrene, polycarbonate, polyurethane, polyethylene, phenolformaldehyde resins, polybutylene, "Teflon", and the like.

The means employed for unsheathing the blade component of the scalpel may be any means whereby the sheath component is retracted to a position uncovering the blade component by depressing an actuating button and thereby causing temporary deformation of an elastic member biased to cause the sheath to return to its original position covering the blade when the actuating button is released. Alternatively, the means employed for unsheathing the blade component may be any means whereby a cantilevered locking mechanism attached to the sheath is released by depressing an actuating button thereby allowing the sheath, button, and locking mechanism to be manually retracted by the operator thereby causing temporary deformation of an elastic member biased to cause the sheath to return to its original resting position covering the blade when the actuating button is released. Typically, the elastic member will be a spring, which is compressed as it is deformed. Alternatively, the elastic member can be stretchable bands which are stretched as they are deformed, or the like. The apparatus of the invention will now be further described and exemplified by reference to the various specific embodiments set forth in the drawings.

Figure 2:
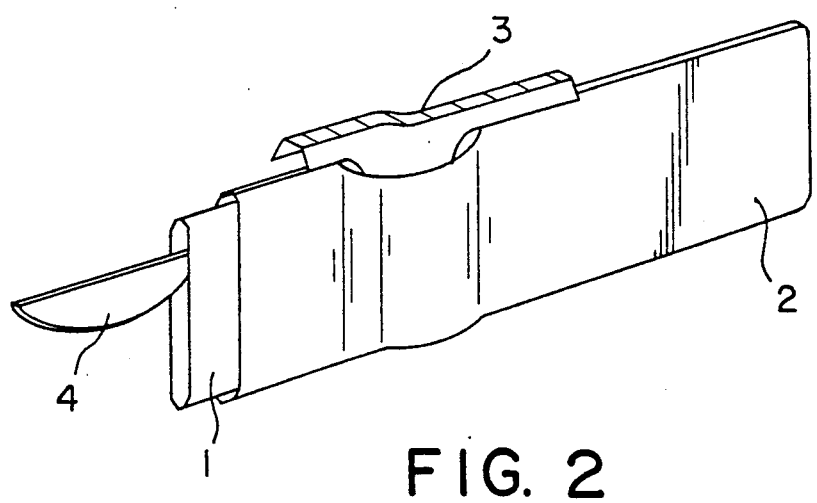
FIG. 2 is a view of the safety scalpel shown in FIG. 1, but with the sheath in a retracted or operating position exposing the cutting blade.

FIG. 1 is an overall view of a disposable embodiment of the invention. As shown in the illustration of FIG. 1, the safety scalpel comprises a handle 2, a scalpel blade 4 mounted at the front end of handle 2, and a protective sheath 1 which can be retracted into handle 2 by depression of the actuator button 3, thereby exposing the scalpel blade 4. The present invention is illustrated in FIG. 2 with its actuator button 3 in the depressed position, and the sheath 1 in its retracted position exposing the scalpel blade 4. The mechanisms allowing retraction of sheath 1 by depression of the actuator button 3, and automatic extension of the sheath 1 to cover the blade 4 upon release of the actuator button 3 will be described in detail below.

FIG. 3 depicts the invention in fully assembled form with a cut-away view which exposes the preferred position of the elastic member 5, typically a spring, as it is positioned relative to the blade holder 6, which holder is affixed to the closed rear end 22 of the handle 2. In a preferred embodiment, the blade holder 6 and handle 2 are of unitary construction, made by injection molding or other techniques well known in the art. Alternatively, the blade holder 6 may be manufactured separately from the handle 2, and later affixed in position during assembly of the safety scalpel. Handle 2 can be made of material in which a phosphorescent component has been included, resulting in a safety scalpel which can be easily seen under darkened conditions due to its luminescent properties. The external surface of handle 2 may comprise a gripping surface, such as ridges, depressions, protuberances, portions which have an increased co-efficient of friction, or other means well known in the art which enhance and facilitate holding the scalpel with one's fingers.

Referring now to FIG. 4, the assembly of the safety scalpel will be described in detail. The handle 2 is a hollow, elongated member which is open at its front end and closed at its rear end 22. Conveniently, the handle 2 will have a substantially rectangular cross-section, or alternatively a substantially oval cross-section, which is slightly larger than the periphery of the sheath 1. In this way, the sheath 1 is free to slide in and out of the handle as will be described in detail below. Handle 2 comprises a blade holder 6 having a blade receiving end 17 in the opening at the front end of the handle 2. The scalpel blade 4 is mounted at the front end of the handle 2 on the blade receiving end 17 by means which are well known in the art. The handle 2 also has an actuator receiving vent 18, which is an opening on the top surface of handle 2 through which the actuator button will be movably disposed once the safety scalpel is assembled. The safety scalpel can be quickly assembled in a preferred embodiment by positioning elastic member 5 inside hollow handle 2 so that it contacts the internal surface of the closed rear end 22 of handle 2, then affixing scalpel blade 4 to the forward blade receiving end 17 of handle 2.

Figure 9A:
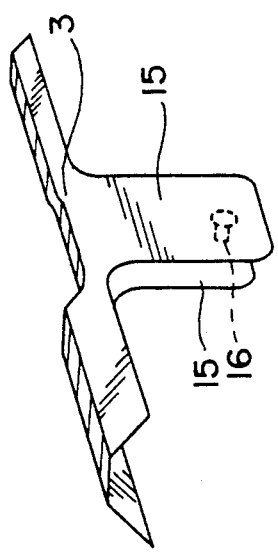
FIG. 9A depicts an oblique view of a preferred embodiment of the actuating button.
Figure 9B:
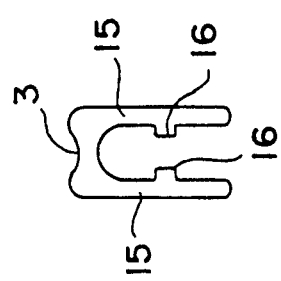
FIG. 9B depicts a front-end-on view of the actuating button depicted in FIG. 9A.

The sheath 1 has a substantially rectangular, or alternatively substantially oval, cross-section which is substantially similar to that of the hollow handle 2, and has an opened front end 11 and an opened rear end 12. In a preferred embodiment, identically positioned grooves 7 are provided in opposite walls of the sheath. The grooves 7 will receive the nipples 16 which are cylindrical protuberances affixed to the internal surfaces of the vertical descending legs 15 attached to the actuator button 3 as shown in FIG. 9, and as described further below. Conveniently, the sheath 1 will be fabricated from a lubricous plastic that will allow the sheath to slide freely in the handle 2 and to allow the nipples 16 to slide freely along the grooves 7. In a preferred embodiment, sheath 1 is constructed of transparent material so the user can see what type of blade is on the scalpel without having to retract the sheath.

Once the elastic member has been disposed inside the hollow handle 2 and the scalpel blade 4 affixed to the blade receiving end 17 of the handle 2, sheath 1 may be inserted rear end first, oriented as depicted in FIG. 4, into the front end of handle 2. Actuator button 3 can be positioned by inserting its vertical descending legs 15 through actuator receiving vent 18 where, in accordance with the properties of the material from which they are manufactured, the vertical descending legs can be outwardly displaced far enough to descend on each side of sheath 1 until the nipples 16 snap into place in the grooves 7 on each side of sheath 1. At this point the assembly of the safety scalpel is complete.

In this embodiment, the safety scalpel can be passed from one person to another without fear of injury from unintentional contact with the blade. The user of the scalpel can, with one hand, simultaneously hold the scalpel and retract the sheath to expose the blade. When the user depresses actuator button 3, nipples 16 travel downward along grooves 7 which causes sheath 1 to move rearward into hollow handle 2, thereby exposing blade 4. As blade 4 is exposed, elastic member 5 is temporarily deformed such that on releasing the pressure applied to actuator button 3, the elastic member relaxes, forcing the nipples 16 upward along groove 7 and extending sheath 1 to cover blade 4 in its resting position.

Figure 8:
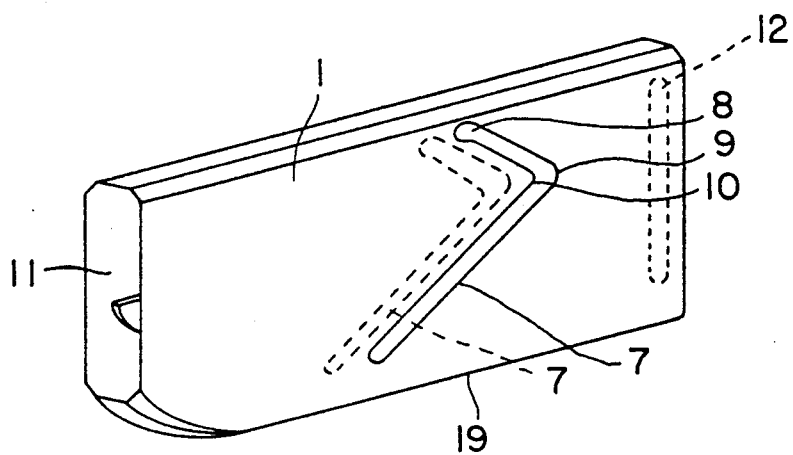
FIG. 8 depicts a preferred embodiment of the sheath, used in the assembly of the scalpel embodiment depicted in FIG. 1.

In its released position the bias of elastic member 5 causes the sheath 1 to be in its extended position covering blade 4. In the embodiment depicted in FIG. 4, nipples 16 will be in contact with groove vertexes 9, and the sheath will be in its maximally extended position. If the sheath is bumped at its front end the sheath may be pushed backward into hollow handle 2, but only for a distance which is insufficient to expose any portion of blade 4. The mechanism by which this is assured is shown in more detail in FIG. 8. Sheath 1 comprises a groove 7, groove vertex 9, safety notch 8, groove flange 10, sheath front opening 11, sheath rear opening 12, and sheath bottom 19. Preferably, there is a groove 7, groove vertex 9, safety notch 8, and groove flange 10 on each side of sheath 1. As measured perpendicularly from sheath bottom 19, groove vertex 9 is located at a higher level on the side of sheath 1 than is groove flange 10. This difference in level allows for sheath 1 to be accidentally bumped at its front opening 11 which displaces sheath 1 rearward into handle 2, but not far enough to expose any portion of blade 4. This is because as sheath 1 moves rearward into handle 2, groove flanges 10 pass underneath nipples 16 which then ride upward into safety notches 8 where they stop the rearward motion of sheath 1 before blade 4 can be exposed.

Figure 5:
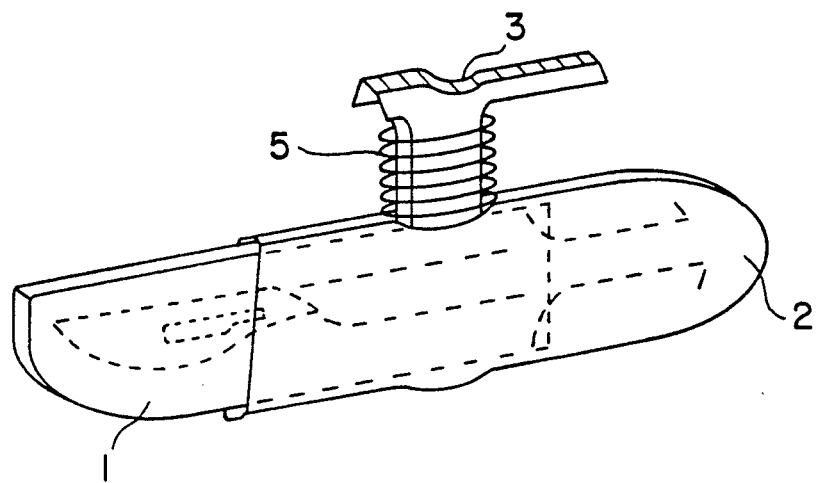
FIG. 5 depicts a alternative embodiment of the assembled scalpel wherein the elastic member is placed in an alternative location.

In an alternative embodiment as depicted in FIG. 5 the elastic member 5 can be positioned external to handle 2 around the vertical descending legs 15 during assembly, which otherwise proceeds as described above. In this embodiment, the elastic member is biased so that actuator button 3 in its resting position is at its furthest possible extension above handle 2. In this position nipples 16 rest in safety notches 8, preventing any rearward motion of sheath 1 to be imparted by accidental contact at sheath front opening 11.

Sheath 1 may also comprise, in an alternative embodiment, bushings or rollers 21 which can contact either the blade holder 6, or alternatively can contact the internal surface of hollow handle 2, to reduce friction or otherwise facilitate retraction and extension of sheath 1 within handle 2.

Figure 10:
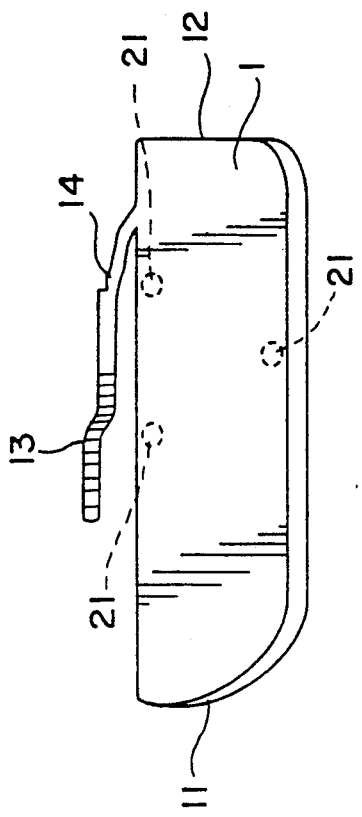
FIG. 10 depicts an alternative embodiment of the sheath, used in the assembly of the scalpel depicted in FIG. 6.
Figure 11:
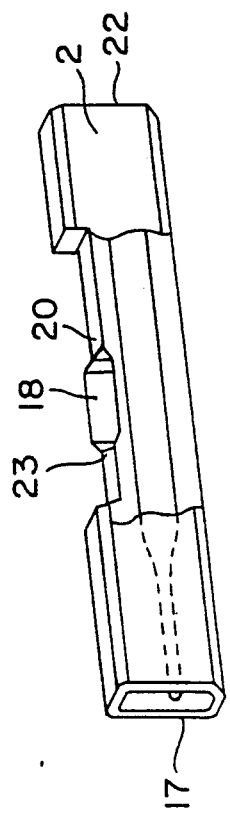
FIG. 11 is a cut-away view of the scalpel handle.

In an alternative embodiment, sheath 1 may be constructed without grooves 7, as depicted in FIG. 10. In this alternative embodiment, an actuator button 13 is connected to sheath lock plate 14 in such a way as to form a cantilevered locking mechanism which itself is affixed to sheath 1. Preferably, in this embodiment the sheath 1 is of unitary construction comprising actuator button 13 and sheath lock plate 14, made by standard molding techniques well known in the art. Assembly of this embodiment is accomplished by positioning elastic member 5 inside handle 2 so that it contacts the internal surface of closed rear end portion 22 of handle 2. Blade 4 is affixed to blade receiving end 17 and the sheath embodiment depicted in FIG. 10 is then passed, rear opening 12 first, over blade 4 and into handle 2. When the sheath has been inserted into handle 2 far enough, the cantilevered locking mechanism comprising actuator button 13 and sheath lock plate 14, typically made from plastic or another resilient material, is forced downward towards the top surface of sheath 1 as it is inserted through the front opening of handle 2 and comes in contact with the upper internal surface of handle 2. As the sheath is pushed farther into handle 2, the cantilevered locking mechanism comprising actuator button 13 and sheath lock plate 14 will encounter actuator receiving vent 18, and, no longer being depressed by the upper internal surface of handle 2, will snap back up into its relaxed position. At this point sheath lock plate 14 will be disposed to contact stop lip 20, which defines the rearward boundary of actuator receiving vent 18 on the upper surface of handle 2, as the sheath is pushed farther into handle 2. The sheath 1 is prevented from sliding back out the front opening of handle 2 by retaining lip 23, which defines the forward boundary of actuator receiving vent 18 on the upper surface of handle 2, and which will contact the free end of actuator button 13 when the cantilevered locking mechanism is in its relaxed position if the sheath 1 is pushed forward. In this position, accidental bumping of sheath front opening 11 will cause sheath lock plate 14 to contact stop lip 20, thereby preventing sheath 1 from being displaced, and preventing any portion of blade 4 from being exposed.

Figure 6:
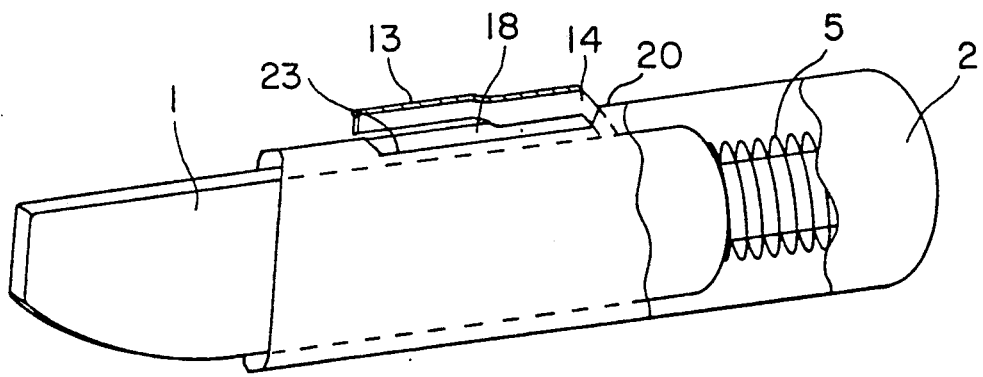
FIG. 6 is a cut-away view of an alternative embodiment of the assembled scalpel with the sheath in its resting position.
Figure 7:
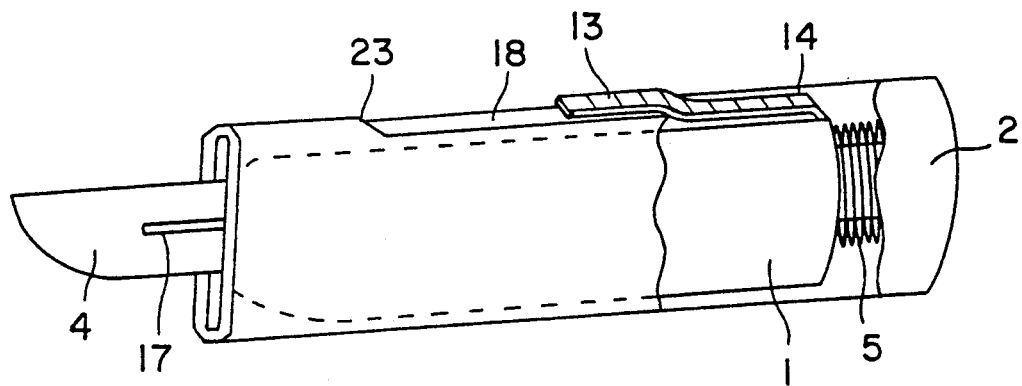
FIG. 7 is a cut-away view of the scalpel depicted in FIG. 6 with the sheath retracted to expose the blade.

In this embodiment, depicted in FIGS. 6 and 7, the safety scalpel can be passed from one person to another without fear of injury from unintentional contact with the blade. The user of the scalpel can hold the scalpel and unsheathe the blade with one hand by depressing actuator button 13 causing downward displacement of sheath lock plate 14 such that it is no longer in contact with stop lip 20, at which point a rearward motion may be imparted by the user to actuator button 13 displacing the sheath rearward inside the hollow handle and temporarily deforming elastic member 5. Upon releasing the pressure applied to actuator button 13, elastic member 5 will relax, forcing the sheath 1 forward to its extended position covering the blade, at which time actuator button 13 and sheath lock plate 14 snap back into their relaxed positions such that sheath lock plate 14 is once again in contact with stop lip 20, and the sheath is thereby locked into position covering the blade.

If the safety scalpel of the subject invention is desired to be used repeatedly, rather than be disposed of after one use, the components may be manufactured from appropriate materials such as surgical steel or other acceptable metals and the like.

Although the foregoing invention has been described in some detail by way of illustration and example, it will be understood that the present invention is not limited to the particular description and specific embodiments described but rather may comprise any combination of the above elements and variations thereof, many of which will be obvious to those skilled in the an in view of this disclosure. Instead, the invention is limited and defined solely by the following claims.

I claim:

1. A safety scalpel comprising:
   a handle having a hollow interior and two opposite ends, said handle having an opening at one of said opposite ends;
   a cutting blade attached to said handle such that a portion of said blade protrudes from said opening;
   a sheath slidably disposed around said cutting blade and within said hollow interior of said handle, said sheath being arranged to reciprocate between an extended position in which said sheath covers said protruding portion of said blade and a retracted position in which said sheath does not cover said protruding portion of said blade so that said protruding portion of said blade is exposed;
   a deformable elastic member disposed so that said elastic member is temporarily deformed when said sheath is in said retracted position and said deformable elastic member relaxes progressively as said sheath is extended, and so that said deformable elastic member continually urges said sheath to said extended position when said sheath is in said retracted position and holds said sheath in said extended position when said sheath is in said extended position; and
   actuating means arranged so as to retract said sheath in response to deliberate actuation of said actuating means, said actuating means further comprising locking means to lock said sheath in said extended position, said locking means arranged to prevent retraction of said sheath and unintentional exposure of said blade resulting from accidental contact with said sheath when said sheath is in said extended position, whereby said scalpel is safe to handle and said cutting blade cannot be exposed by accidentally bumping said sheath when said sheath is in said extended position, but which can easily be used and said blade can easily be exposed by actuating said actuating means.

2. The safety scalpel of claim 1 wherein said sheath comprises a bushing or roller.

3. The safety scalpel of claim 1 wherein said actuating means comprises a vertical descending leg.

4. The safety scalpel of claim 3 wherein said vertical descending leg comprises a nipple.

5. The safety scalpel of claim 1 wherein said actuating means comprises a cantilevered locking mechanism.

6. The safety scalpel of claim 1 wherein the deformable elastic member is a coil spring.

7. The safety scalpel of claim 1 wherein the deformable elastic member is a stretchable band.

* * * * *

UNITED STATES PATENT AND TRADEMARK OFFICE
CERTIFICATE OF CORRECTION

PATENT NO. : 5,330,492
DATED : July 19, 1994
INVENTOR(S) : Doug L. Haugen

It is certified that error appears in the above-indentified patent and that said Letters Patent is hereby corrected as shown below:

Column 1, line 40: After "disposable items" insert --.--

Column 2, line 11: Delete "fury" and insert --fully--.

Column 6, line 33: Delete "in the an in view" and insert --in the art in view--.

Signed and Sealed this

Twentieth Day of September, 1994

Attest:

BRUCE LEHMAN

Attesting Officer     Commissioner of Patents and Trademarks